United States Patent
Kobayashi et al.

(10) Patent No.: US 11,627,240 B2
(45) Date of Patent: Apr. 11, 2023

(54) IMAGE PICKUP APPARATUS FOR ENDOSCOPE, ENDOSCOPE, AND METHOD OF PRODUCING IMAGE PICKUP APPARATUS FOR ENDOSCOPE

(71) Applicant: OLYMPUS CORPORATION, Tokyo (JP)

(72) Inventors: Hiroshi Kobayashi, Nagano (JP); Takatoshi Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 207 days.

(21) Appl. No.: 16/921,236

(22) Filed: Jul. 6, 2020

(65) Prior Publication Data
US 2020/0333581 A1  Oct. 22, 2020

Related U.S. Application Data

(63) Continuation of application No. PCT/JP2018/044667, filed on Dec. 5, 2018.

(30) Foreign Application Priority Data

Jan. 9, 2018  (WO) .................. PCT/JP2018/000181

(51) Int. Cl.
*H04N 5/225* (2006.01)
*G02B 23/24* (2006.01)
*A61B 1/04* (2006.01)

(52) U.S. Cl.
CPC .............. *H04N 5/2254* (2013.01); *A61B 1/04* (2013.01); *G02B 23/2423* (2013.01);
(Continued)

(58) Field of Classification Search
CPC ............ G02B 23/2484; G02B 23/2423; G02B 23/243; G02B 23/2446; H04N 5/2257;
(Continued)

(56) References Cited

U.S. PATENT DOCUMENTS

2011/0074941 A1* 3/2011 Takasaki .................. A61B 1/05
                                                                 348/E7.085
2012/0206583 A1* 8/2012 Hoshi ................ G02B 23/2469
                                                                       348/76
(Continued)

FOREIGN PATENT DOCUMENTS

EP          2858105 A1    4/2015
JP       2005-334509 A   12/2005
(Continued)

OTHER PUBLICATIONS

International Search Report dated Feb. 26, 2019 issued in PCT/JP2018/044667.

*Primary Examiner* — Aaron B Fairchild
*Assistant Examiner* — Christen A. Sharpless
(74) *Attorney, Agent, or Firm* — Scully, Scott, Murphy & Presser, P.C.

(57) ABSTRACT

An image pickup apparatus for endoscope includes: an optical unit having an incident surface and an emitting surface; an image pickup unit adhering to the emitting surface; an interposer where the image pickup unit is bonded to a first electrode of a first main surface; and an electric cable bonded to the interposer. The image pickup unit is smaller than the optical unit and the interposer in an outer size in a direction orthogonal to an optical axis. The image pickup apparatus for endoscope further includes a heat conductive resin with which a portion among the emitting surface, the first main surface, and a side surface of the image pickup unit is filled. The first electrode extends to a position where the first electrode is brought into contact with the heat conductive resin.

9 Claims, 8 Drawing Sheets

(52) U.S. Cl.
CPC ....... *G02B 23/2484* (2013.01); *H04N 5/2257* (2013.01); *H04N 2005/2255* (2013.01)

(58) Field of Classification Search
CPC ......... H04N 2005/2255; H04N 5/2253; H04N 5/2254; A61B 1/04; A61B 1/05
See application file for complete search history.

(56) References Cited

U.S. PATENT DOCUMENTS

| | | | |
|---|---|---|---|
| 2012/0318572 A1* | 12/2012 | Ishii | H05K 3/3436 |
| | | | 174/260 |
| 2015/0085094 A1 | 3/2015 | Fujimori et al. | |
| 2016/0029879 A1* | 2/2016 | Ishikawa | A61B 1/051 |
| | | | 600/110 |
| 2018/0303325 A1 | 10/2018 | Fujimori et al. | |

FOREIGN PATENT DOCUMENTS

| | | | |
|---|---|---|---|
| JP | 2011-200399 A | | 10/2011 |
| JP | 2011-243596 A | | 12/2011 |
| JP | 2013-30593 A | | 2/2013 |
| JP | 2014-110847 A | | 6/2014 |
| JP | 2014110847 A | * | 6/2014 |
| JP | 2015-198805 A | | 11/2015 |
| WO | WO 2013/179766 A1 | | 12/2013 |
| WO | WO 2017/072847 A1 | | 5/2017 |
| WO | WO 2017/073440 A1 | | 5/2017 |
| WO | WO 2017/179144 A1 | | 10/2017 |
| WO | WO 2017/203593 A1 | | 11/2017 |
| WO | WO 2018/173323 A1 | | 9/2018 |
| WO | WO 2018/194039 A1 | | 10/2018 |

\* cited by examiner

IMAGE PICKUP APPARATUS FOR ENDOSCOPE, ENDOSCOPE, AND METHOD OF PRODUCING IMAGE PICKUP APPARATUS FOR ENDOSCOPE

CROSS REFERENCE TO RELATED APPLICATION

This application is a continuation application of PCT/JP2018/044667 filed on Dec. 5, 2018 and claims benefit of PCT/JP2018/000181 filed on Jan. 9, 2018, the entire contents of which are incorporated herein by this reference.

BACKGROUND OF THE INVENTION

1. Field of the Invention

The present invention relates to an image pickup apparatus for endoscope including an optical unit and an image pickup unit, an endoscope including an image pickup apparatus which includes an optical unit and an image pickup unit, and a method of producing an image pickup apparatus for endoscope including an optical unit and an image pickup unit.

2. Description of the Related Art

An image pickup signal which an image pickup device disposed on a distal end portion of an endoscope outputs is processed through primary processing by a plurality of electronic components and the processed signal is transmitted thereafter.

For example, Japanese Patent Application Laid-Open Publication No. 2005-334509 discloses an endoscope having an image pickup apparatus which transmits an image pickup signal which is processed through primary processing by a plurality of electronic components mounted on a wiring board via an electric cable.

Japanese Patent Application Laid-Open Publication No. 2013-30593 discloses a stacked device which is formed by stacking a plurality of semiconductor devices for housing a plurality of semiconductor devices in a small space and for reducing a parasitic capacitance generated by wiring International Publication No 2017/073440 discloses an endoscope which realizes downsizing and sophistication of functions of an image pickup apparatus by using a stacked device.

An electric cable or a wiring board is connected to an image pickup apparatus for transmitting an image pickup signal or for supplying a drive power source to the image pickup apparatus. In the image pickup apparatus which includes a stacked device, the electric cable or the like and the stacked device are bonded to each other. The image pickup apparatus to which the electric cable or the like is bonded is disposed on a distal end portion of an endoscope in an assembling step.

Japanese Patent Application Laid-Open Publication No. 2015-198805 discloses an image pickup apparatus where a sealing resin is disposed on a side surface of an image pickup device disposed between a cover member and a substrate. With the use of the sealing resin including a filler which has high heat conductivity, heat generated from an image pickup device is radiated through the sealing resin.

SUMMARY OF THE INVENTION

An image pickup apparatus for endoscope according to an embodiment includes: an optical unit formed by stacking a plurality of optical members, the optical unit including an incident surface and an emitting surface; an image pickup unit including a front surface which opposedly faces the emitting surface and a rear surface on a side opposite to the front surface, wherein an external electrode which is connected to a light receiving portion via a first penetration wire is disposed on the rear surface; an interposer including a first main surface and a second main surface on a side opposite to the first main surface, wherein a first electrode is disposed on the first main surface, a second electrode which is connected to the first electrode via a second penetration wire is disposed on the second main surface, and the first electrode is bonded to the external electrode; and an electric cable or a wiring board bonded to the second electrode by soldering. The image pickup unit is smaller than the optical unit and the interposer in an outer size in a direction orthogonal to an optical axis, and the image pickup unit is housed in a space disposed on an imaginary extension of the optical unit in an optical axis direction, the image pickup apparatus further includes a heat conductive resin with which a portion among the emitting surface, the first main surface, and a side surface of the image pickup unit is filled, and the first electrode extends to a position where the first electrode is brought into contact with the heat conductive resin.

An endoscope according to the embodiment includes an image pickup apparatus. The image pickup apparatus includes: an optical unit formed by stacking a plurality of optical members, the optical unit including an incident surface and an emitting surface; an image pickup unit including a front surface which opposedly faces the emitting surface and a rear surface on a side opposite to the front surface, wherein an external electrode which is connected to a light receiving portion via a first penetration wire is disposed on the rear surface; an interposer including a first main surface and a second main surface on a side opposite to the first main surface, wherein a first electrode is disposed on the first main surface, a second electrode which is connected to the first electrode via a second penetration wire is disposed on the second main surface, and the first electrode is bonded to the external electrode; and an electric cable or a wiring board bonded to the second electrode by soldering. The image pickup unit is smaller than the optical unit and the interposer in an outer size in a direction orthogonal to an optical axis, and the image pickup unit is housed in a space disposed on an imaginary extension of the optical unit in an optical axis direction, the image pickup apparatus further includes a heat conductive resin with which a portion among the emitting surface, the first main surface, and a side surface of the image pickup unit is filled, and the first electrode extends to a position where the first electrode is brought into contact with the heat conductive resin.

A method of producing an image pickup apparatus for endoscope according to the embodiment includes: manufacturing an optical unit formed by stacking a plurality of optical members and including an incident surface and an emitting surface; manufacturing an image pickup unit including a front surface and a rear surface on a side opposite to the front surface, wherein an external electrode which is connected to a light receiving portion via a first penetration wire is disposed on the rear surface; manufacturing an interposer including a first main surface and a second main surface on a side opposite to the first main surface, wherein a first electrode is disposed on the first main surface, and a second electrode which is connected to the first electrode via a second penetration wire is disposed on the second main surface; making the optical unit adhere to the front surface of the image pickup unit; bonding the external electrode of the image pickup unit and the first electrode of the interposer to each other; bringing a portion of the first electrode into contact with a heat conductive resin by filling, with the heat conductive resin, a portion among a side surface of the image pickup unit which is smaller than the optical unit and the interposer in an outer size in a direction orthogonal to an optical axis, and is housed in a space disposed on an imaginary extension of the optical unit in an optical axis direction, the emitting surface, and the first main surface; and bonding an electric cable or a wiring board to the second electrode.

DETAILED DESCRIPTION OF THE PREFERRED EMBODIMENTS

<Configuration of Endoscope>

Figure 1:
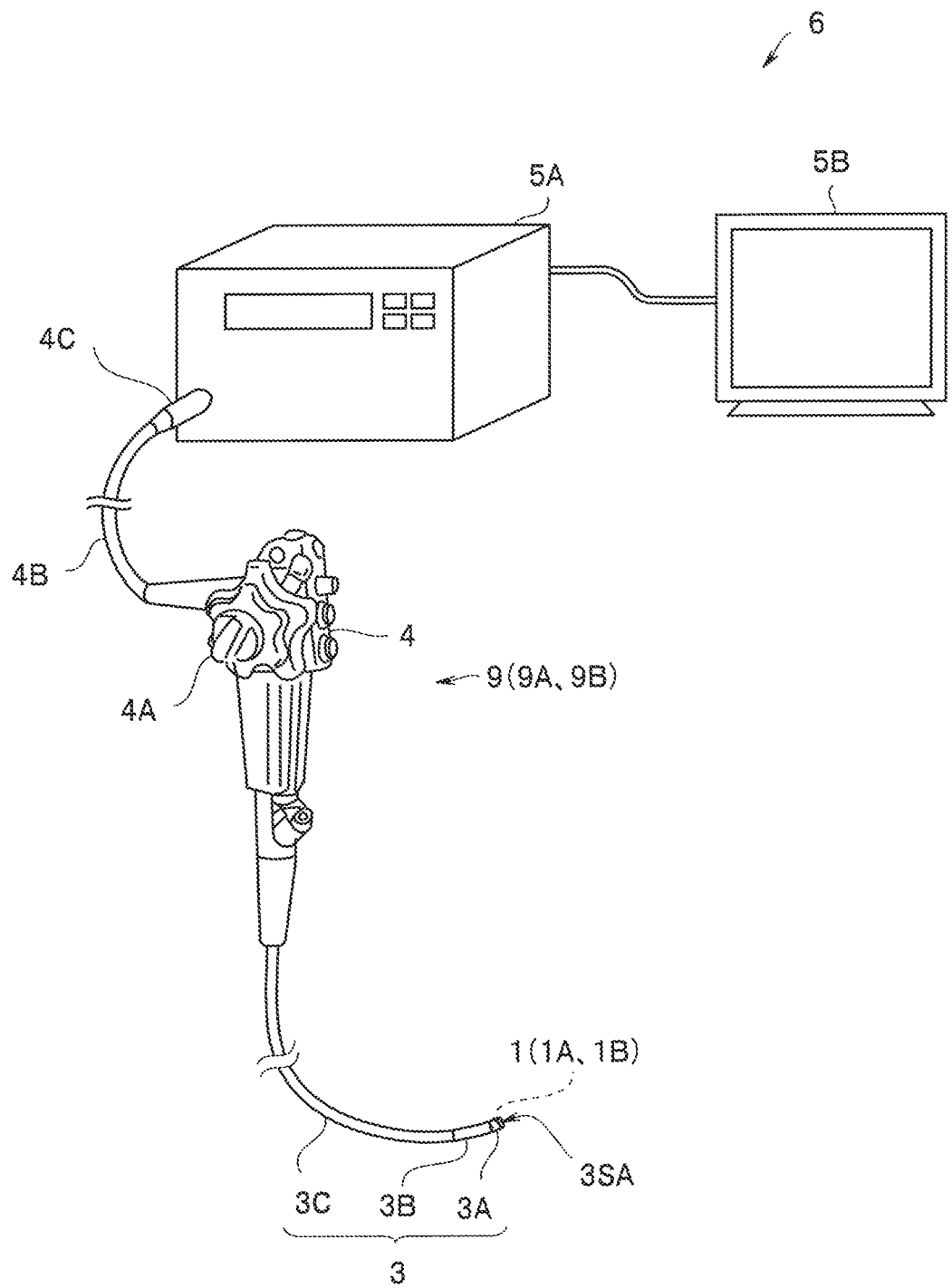
FIG. 1 is a perspective view of an endoscope according to an embodiment.

An endoscope 9 according to an embodiment shown in FIG. 1 forms an endoscope system 6 together with a processor 5A and a monitor 5B. In the endoscope 9, an image pickup apparatus for endoscope (hereinafter, also referred to as "image pickup apparatus") is disposed on a distal end portion 3A of an insertion section 3.

The endoscope 9 includes: the insertion section 3; a grasping section 4 disposed on a proximal end portion side of the insertion section 3; a universal cord 4B extending from the grasping section 4; and a connector 4C disposed on a proximal end portion side of the universal cord 4B. The insertion section 3 includes: the distal end portion 3A on which the image pickup apparatus 1 is disposed; a bending portion 3B extending toward a proximal end side of the distal end portion 3A and being bendable for changing a direction of the distal end portion 3A; and a flexible portion 3C extending toward a proximal end side of the bending portion 3B. A rotatable angle knob 4A which is an operation portion operated by a surgeon for operating the bending portion 3B is disposed on the grasping section 4.

The universal cord 4B is connected to the processor 5A via the connector 4C. The processor 5A controls an entire endoscope system 6, and applies signal processing to an image pickup signal outputted from the image pickup apparatus 1, and outputs the processed signal as an image signal. The monitor 5B displays the image signal which the processor 5A outputs as an endoscope image. Although the endoscope 9 is a flexible endoscope in the embodiment, an endoscope according to the present invention may be a rigid endoscope, and is used both in a medical field and in an industrial field.

As described later, the image pickup apparatus 1 for endoscope is small-sized and is highly reliable. The endoscope 9 having the distal end portion 3A on which the image pickup apparatus 1 for endoscope is disposed is highly reliable, and the distal end portion 3A is a narrow diameter and hence, the endoscope 9 exhibits low invasion.

First Embodiment

Figure 2:
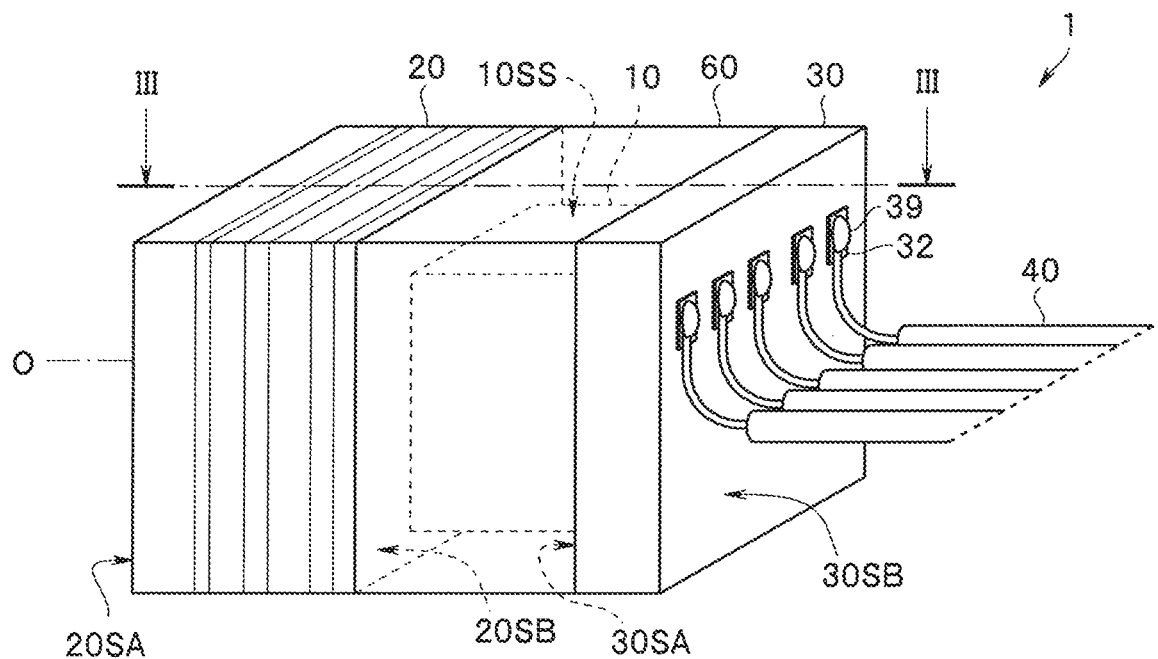
FIG. 2 is a perspective view of the image pickup apparatus according to a first embodiment.
Figure 3:
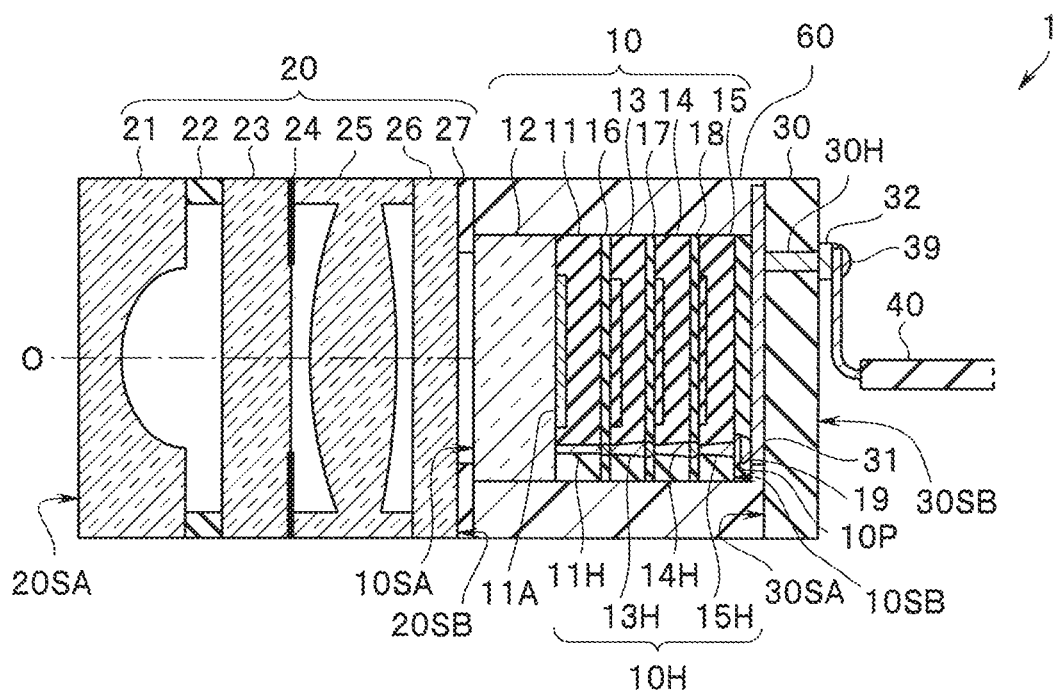
FIG. 3 is a cross-sectional view of the image pickup apparatus according to the first embodiment taken along a line III-III in FIG. 2.

The image pickup apparatus 1 for endoscope of this embodiment shown in FIG. 2 and FIG. 3 includes an image pickup unit 10; an optical unit 20; an interposer 30, a heat conductive resin 60, and electric cables 40. The image pickup apparatus 1 receives an image pickup light which is a light converged by the optical unit 20, converts the image pickup light into an electric signal, and outputs the electric signal to the processor 5A via the electric cables 40 after applying primary processing to the electric signal.

Drawings based on the respective embodiments are schematic views. Accordingly, note that a relationship between a thickness and a width of each member, a ratio between thicknesses, a relative angle and the like of respective members differ from the corresponding relationships of members of an actual image pickup apparatus. There may be a case where portions of the image pickup apparatus are described with different size relationship or different ratios among the drawings. There may be also a case where some constitutional components are not illustrated or symbols are not given to some constitutional components. A direction along which an object whose image is to be picked up is referred to as a frontward direction.

The optical unit 20 formed by stacking a plurality of optical members 21 to 27 is a rectangular parallelepiped body having an incident surface 20SA on which light is incident and an emitting surface 20SB disposed on an opposite side of the incident surface 20SA.

The optical members 21 and 25 are lenses, the optical members 22 and 27 are spacers, the optical member 23 is a filter, the optical member 24 is an aperture, and the optical member 26 is a protective glass. The number, the arrangement and the like of the optical members are set corresponding to a specification of the optical unit.

The image pickup unit 10 includes a cover glass 12, an image pickup device 11, a stacked element formed by stacking a plurality of semiconductor devices 13, 14, and 15. The image pickup unit 10 is a rectangular parallelepiped body having a front surface 10SA, a rear surface 10SB disposed on a side opposite to the front surface 10SA, and four side surfaces 10SS. The image pickup unit 10 is formed such that the front surface 10SA is disposed so as to opposedly face the emitting surface 20SB of the optical unit 20 and adheres to the emitting surface 20SB.

The image pickup device 11 has a light receiving portion 11A formed of a CCD or CMOS, and the light receiving portion 11A is connected to penetration wires 11H. The image pickup device 11 may be either a front-illuminated image sensor or a back-illuminated image sensor.

The cover glass 12 adheres to the image pickup device 11 using an adhesive agent (not shown in the drawings). Although the cover glass 12 protects the light receiving portion 11A in producing steps, the cover glass 12 is not an indispensable constitutional component for forming the image pickup unit 10. The cover glass 12 is not limited to a parallel planar plate made of glass, and may be a resin plate, a ceramic plate or the like having high optical transmissivity with respect to an image pickup light.

The semiconductor devices 13 to 15 of the image pickup unit 10 have penetration wires 13H to 15H respectively, and the semiconductor devices 13 to 15 are electrically connected to each other. The image pickup device 11 and the semiconductor devices 13 to 15 are connected to each other via a solder bump formed by an electroplating method or via a solder bonding portion made of a solder paste film formed by printing or the like.

A sealing resin 16 is disposed between the image pickup device 11 and the semiconductor device 13, a sealing resin 17 is disposed between the semiconductor device 13 and the semiconductor device 14, and a sealing resin 18 is disposed between the semiconductor device 14 and the semiconductor device 15. The image pickup unit 10 applies primary processing to an image pickup signal outputted from the image pickup device 11, or applies processing to a control signal controlling the image pickup device 11. For example, the semiconductor devices 13 to 15 include an AD convertor, a memory, a transmission output circuit, a filter circuit, a thin film capacitor, and a thin film inductor. The number of devices which the image pickup unit 10 includes is 2 to 10 including the image pickup device 11, for example. The image pickup apparatus 1 which includes the stacked element is small-sized and has high functions.

A plurality of external electrodes 10P are disposed on the rear surface 10SB of the image pickup unit 10 (a rear surface of the semiconductor device 15 which is stacked on a rearmost portion). The external electrode 10P is, for example, formed of a barrier Ni layer and an Au layer disposed on a wiring pattern made of Cu. The external electrodes 10P are electrically connected to the light receiving portion 11A via first penetration wires 10H (11H and 13H to 15H).

The interposer 30 is a parallel planar plate which includes a first main surface 30SA, a second main surface 30SB disposed on a side opposite to the first main surface 30SA. A plurality of first electrodes 31 are disposed on the first main surface 30SA, and a plurality of second electrodes 32 which are electrically connected to the respective first electrodes 31 via the respective second penetration wires 30H are disposed on the second main surface 30SB.

The first electrodes 31 electrically connect the first penetration wires 10H and the second penetration wires 30H. In other words, the first electrodes 31 are elongated conductor patterns extending from a position where the first electrodes 31 opposedly face the first penetration wires 10H to a position where the first electrodes 31 opposedly face the second penetration wires 30H. The first electrodes 31 and the second electrodes 32 are made of gold, copper, aluminum or the like.

The first electrodes 31 further extend from the position where the first electrodes 31 are connected to the second penetration wires 30H to an end surface of the first main surface 30SA. As described later, it is preferable that at least a portion of each first electrode 31 extend to a position where such a portion is brought into contact with the heat conductive resin 60. However, such a portion may not extend to the position.

First bonding portions between the first electrodes 31 and the external electrodes 10P of the image pickup unit 10 are, for example, solder bonding portions via first solders 19 or heat ultrasonic bonding portions to which both ultrasonic waves and heat are applied. On the other hand, second bonding portions between the second electrodes 32 and the electric cables 40 are solder bonding portions via second solders 39 or heat ultrasonic bonding portions.

In bonding the second bonding portions, to prevent melting of the first solders 19 of the first bonding portions which are already bonded, it is preferable that a melting point of the second solders 39 be lower than a melting point of the first solders 19.

The interposer 30 is disposed between the image pickup unit 10 and the electric cables 40, and electrically connects the image pickup unit 10 and the electric cables 40 to each other. The interposer 30 is an MID (molded interconnect device), a ceramic substrate, a silicon substrate, a glass substrate or the like. When the electric cables 40 are directly bonded to the image pickup unit 10, a mechanical load and a thermal load are applied to the image pickup unit 10 and hence, there is a risk that reliability of the image pickup apparatus 1 is lowered. By electrically connecting the image pickup unit 10 and the electric cables 40 via the interposer 30, the reliability of the image pickup unit 10 can be ensured.

As described later, the electric cables 40 may be electrically connected to the interposer 30 via a wiring board. In other words, the second electrodes 32 of the interposer 30 may be bonded to a wiring board by the second solders 39, and the electric cables 40 may be connected to the wiring board.

An outer size of the rear surface 10SB (front surface 10SA) of the image pickup unit 10 is set smaller than an outer size of the emitting surface 20SB (incident surface 20SA) of the optical unit 20 and an outer size of the first main surface 30SA (second main surface 30SB) of the interposer 30. In other words, the image pickup unit 10 is smaller than the optical unit 20 and the interposer 30 in an outer size in a direction orthogonal to an optical axis. The image pickup unit 10 and the optical unit 20 are disposed in a state where an optical axis O of the image pickup unit 10 and an optical axis O of the optical unit 20 agree with each other. The interposer 30 is also disposed in a state where a center axis of the interposer 30 substantially agrees with the optical axis O.

In the image pickup apparatus 1, the outer size of the optical unit 20 is set substantially equal to the outer size of the interposer 30. However, the outer size of the optical unit 20 may be set larger than the outer size of the interposer 30.

The image pickup unit 10 is housed in a space disposed on an imaginary extension of the optical unit 20 in an optical axis direction. A portion among the emitting surface 20SB, the first main surface 30SA, and four side surfaces 10SS of the image pickup unit 10 is filled with the heat conductive resin 60.

Heat conductivity of a general resin is less than 0.5 W/mK, for example. On the other hand, heat conductivity of the heat conductive resin 60 containing a filler of high heat conductivity is a value which is more than 1 W/mK, and preferably a value which is more than 5 W/mK.

The heat conductive resin 60 efficiently transfers heat which the image pickup unit 10 generates and radiates such heat and hence, the image pickup unit 10 exhibits high reliability in use. Further, as described later, in a case where the second electrodes 32 and the electric cables 40 are bonded to each other by soldering (second bonding step, see FIG. 4), a stress is applied to the stacked element having a mechanical strength which is not so high or heat is applied to the image pickup unit 10, particularly to the first bonding portions between the external electrodes 10P and the first electrodes 31 and hence, reliability of the image pickup unit 10 is lowered. The heat conductive resin 60 can prevent such lowering of the reliability of the image pickup unit 10.

Further, the heat conductive resin 60 improves the reliability of the image pickup apparatus 1 by preventing infiltration of moisture from the side surfaces of the image pickup unit 10. Still further, in a case where the heat conductive resin 60 is a light shielding resin, it is possible to prevent an external light from entering the light receiving portion 11A of the image pickup device 11.

The image pickup apparatus 1 includes the image pickup unit 10 formed by stacking the plurality of semiconductor devices 13 to 15 and hence, the image pickup apparatus 1 is small-sized and has high functions. Further, the image pickup apparatus 1 includes the heat conductive resin 60 and hence, there is no possibility that the image pickup apparatus 1 is broken during the production of the image pickup apparatus 1 as described later, and the image pickup apparatus 1 exhibits high reliability.

The case is considered where a resin, heat conductivity of which is not so high, is formed on four side surfaces 10SS of the image pickup unit 10 in place of the heat conductive resin 60. Even in such a case, a mechanical strength of the image pickup apparatus is enhanced. Accordingly, such an image pickup apparatus is not broken during the production of the image pickup apparatus. Further, needless to say, infiltration of moisture into the image pickup apparatus from side surfaces is prevented and hence, the image pickup apparatus exhibits high reliability.

<Method of Producing an Image Pickup Apparatus>

Figure 4:
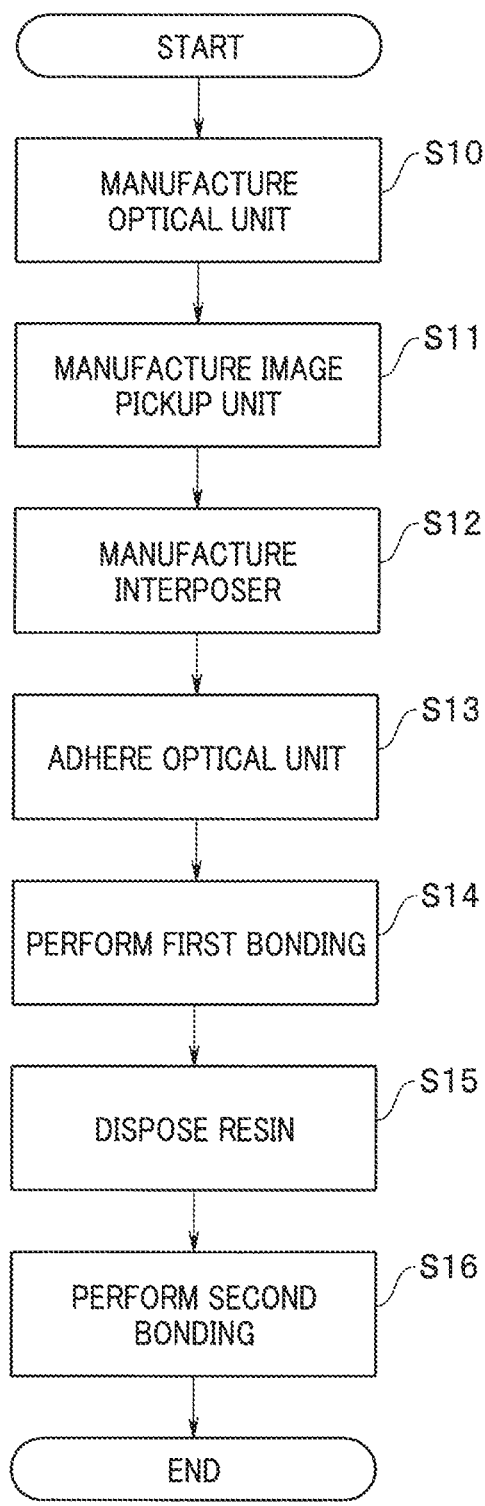
FIG. 4 is a flowchart of a method of producing an image pickup apparatus according to the first embodiment.

A method of producing the image pickup apparatus 1 for endoscope is simply described in accordance with a flowchart shown in FIG. 4.

<Step S10> Optical Unit Manufacturing Step

A plurality of optical wafers (not shown in the drawings) each of which includes the plurality of optical members 21 to 27 are manufactured. For example, a transparent resin which is disposed on a glass wafer is subjected to curing treatment in a state where an outer surface shape of the transparent resin is defined by a lens mold. An optical wafer may be manufactured by sandwiching a resin wafer between two lens molds and by molding the resin wafer while supplying heat.

An optical bonding wafer formed by adhering the plurality of optical wafers is cut so that a plurality of individual optical units 20 which are rectangular parallelepiped bodies are obtained. In other words, the optical units 20 are manufactured by a wafer leveling method. Four side surfaces of the optical unit 20 manufactured by the wafer leveling method are cut sections. Cutting may be performed by blade dicing in general. However, laser dicing or plasma dicing may be adopted.

<Step S11> Image Pickup Unit Manufacturing Step

An image pickup wafer (not shown in the drawing) which includes the plurality of image pickup devices 11, and a plurality of semiconductor wafers (not shown in the drawing) each including the plurality of semiconductor devices 13 to 15 are manufactured.

A plurality of light receiving portions 11A and the like are disposed on the image pickup wafer by applying a known semiconductor producing technique to a silicon wafer. A peripheral circuit which applies primary processing to an output signal of the light receiving portion 11A and processes a drive control signal may be formed on the image pickup wafer. It is preferable that a cover glass wafer which protects the light receiving portions 11A adhere to the image pickup wafer using an adhesive agent (not shown in the drawing) before the through holes (penetration wires 11H) are formed in the image pickup wafer by etching from a rear surface.

Then, the image pickup wafer to which the cover glass wafer adheres and the plurality of semiconductor wafers each including the plurality of semiconductor devices 13 to 15 are stacked to each other with the sealing resins 16 to 18 sandwiched therebetween thus manufacturing the semiconductor bonding wafer. The sealing resins 16 to 18 may be injected from a side surface of the bonding wafer after the plurality of semiconductor wafers are bonded to each other, or disposed at the time of stacking the image pickup wafer and the plurality of semiconductor wafers. It is preferable that the sealing resins 16 to 18 exhibit excellent moisture resistance and have substantially the same thermal expansion coefficient as the semiconductor device 13 or the like.

The plurality of individual image pickup units 10 which are rectangular parallelepiped bodies are obtained by cutting the semiconductor bonding wafer such that four sides of the approximately rectangular light receiving portion 11A of the image pickup device 11 are respectively arranged parallel to four sides of a rectangular cross section of the cut stacked element orthogonal to the optical axis O. Four side surfaces of the image pickup unit 10 manufactured by a wafer leveling method are cut sections.

In accordance with the above-mentioned step, the image pickup unit 10 is manufactured where the image pickup unit 10 includes the front surface 10SA and the rear surface 10SB on a side opposite to the front surface 10SA, the cover glass 12, the image pickup device 11, and the plurality of semiconductor devices 13 to 15 are stacked, and the external electrodes 10P are disposed on the rear surface 10SB.

<Step S12> Interposer Manufacturing Step

The interposer 30 is manufactured where the interposer 30 includes the first main surface 30SA and the second main surface 30SB, the first electrodes 31 are disposed on the first main surface 30SA, and the second electrodes 32 which are connected to the first electrodes 31 via the second penetration wires 30H are disposed on the second main surface 30SB.

The interposer 30 is a wiring board made of ceramic, silicon, glass or the like. The interposer 30 may be manufactured by cutting an interposer wafer including the plurality of interposers 30 using wafer leveling method.

The order that the optical unit manufacturing step (S10), the image pickup unit manufacturing step (S11), and the interposer manufacturing step (S12) are performed may differ from the above-mentioned order. The interposer manufacturing step (S12) may be performed as the first step.

Although the image pickup unit 10, the optical unit 20, and the interposer 30 are rectangular parallelepiped bodies, corner portions of the image pickup unit 10, the optical unit 20, or the interposer 30 which are parallel to the optical axis O after cutting may be chamfered thus forming a cross-section in a direction orthogonal to the optical axis into a hexagonal shape, or the corner portions may be formed into a curved shape.

<Step S13> Optical Unit Adhering Step

The front surface 10SA of the image pickup unit 10 and the emitting surface 20SB of the optical unit 20 are aligned with each other along an optical axis, and are made to adhere to each other using an adhesive agent (not shown in the drawings).

<Step S14> First Bonding Step

Figure 5:
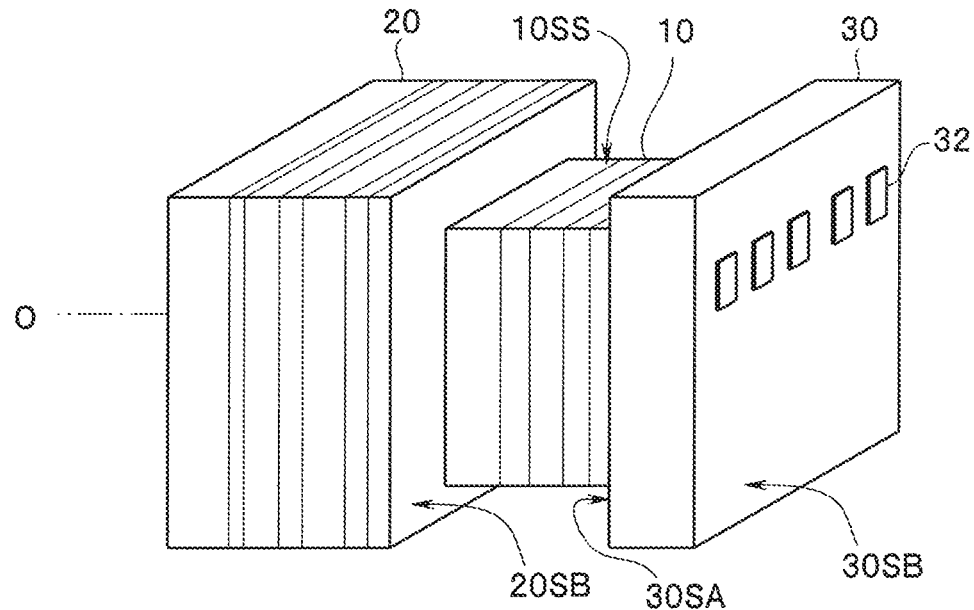
FIG. 5 is a perspective view for describing the method of producing an image pickup apparatus according to the first embodiment.

As shown in FIG. 5, the rear surface 10SB of the image pickup unit 10 is disposed so as to opposedly face the first main surface 30SA of the interposer 30, and bonding at the first bonding portions between the external electrodes 10P and the first electrodes 31 is performed using the first solders 19. The first solders 19 are disposed in advance at least on the external electrodes 10P and on the first electrode 31.

For example, the rear surface 10SB of the image pickup unit 10 is disposed on the first main surface 30SA of the interposer 30 in a state where the second main surface 30SB of the interposer 30 is brought into contact with a heat generating surface of a heater such as a hot plate. When the second main surface 30SB is heated by face heating, the first solders 19 are melted and the external electrodes 10P and the first electrodes 31 are bonded to each other.

Heat generated by the heater is transferred to the first solders 19 through the second electrodes 32, the second penetration wires 30H, and the first electrodes 31 of the interposer 30. Heat conductivity of a substrate of the interposer 30 is smaller than heat conductivity of a conductor and hence, heat is mainly transferred through the second penetration wires 30H, the first electrodes 31 and the like which exhibit high heat conductivity.

The order that the optical unit adhering step (S13) and the first bonding step (S14) are performed may differ from the above-mentioned order. In other words, the first bonding step (S14) may be performed prior to the optical unit adhering step (S13).

<Step S15> Resin Disposing Step

Figure 6:
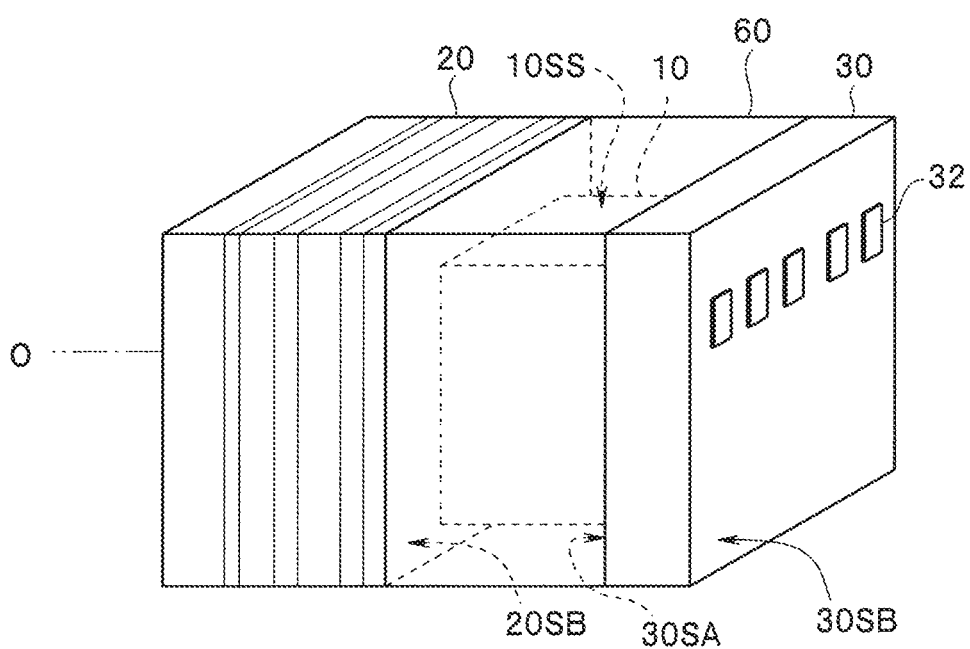
FIG. 6 is a perspective view for describing the method of producing an image pickup apparatus according to the first embodiment.

As shown in FIG. 6, after the first bonding step, a portion among the emitting surface 20SB, the first main surface 30SA, and four side surfaces 10SS of the image pickup unit 10 is filled with the heat conductive resin 60. For example, the uncured heat conductive resin 60 is injected onto four side surfaces 10SS, and the heat conductive resin 60 is cured and solidified by heat treatment at a temperature of approximately 100° C.

The heat conductive resin 60 is disposed only in the space disposed on the imaginary extension of the optical unit 20 in an optical axis direction and hence, an outer size of the image pickup apparatus is not increased.

The heat conductive resin 60 is formed by mixing a filler having high heat conductivity into a resin.

As such a resin, for example, an epoxy resin, a polyimide resin, a fluororesin, polyamide imide, polyphenylene ether, polypropylene, polysulfone, polyethersulfone, polyetheretherketone, polyether ketone, polyetherimide, fluorine thermoplastic elastomer, or butadiene rubber can be used. The resin may be a same resin used as the sealing resins 16 to 18.

As the filler, metal, a ceramic material or the like having higher heat conductivity than a resin, preferably, heat conductivity more than 10 W/mK can be used. As the filler, $SiO_2$, SiC, AlN, ZnO, $Si_3N_4$, BN, $Al_2O_3$, Cu, Al, Ni, Mg, Ag, Bi, Zn, Sn, or C (carbon) can be exemplified. Heat conductivities of AlN, $Si_3N_4$, Cu, and C are respectively 300 W/mK, 80 W/mK, 400 W/mK, and 200 to 1500 W/mK.

It is preferable that the content of the filler be more than 50 weight % for setting heat conductivity of the heat conductive resin 60 to more than 1 W/mK. It is preferable that the content of the filler be less than 70 weight % for maintaining adhesiveness of the filler.

<Step S16> Second Bonding Step

Figure 7:
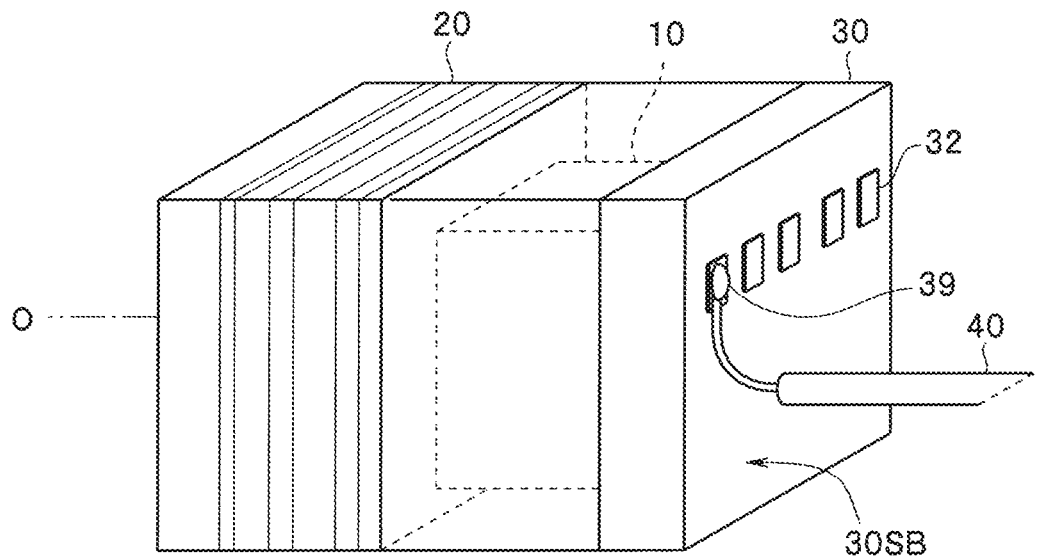
FIG. 7 is a perspective view for describing the method of producing an image pickup apparatus according to the first embodiment.

As shown in FIG. 7, the second electrodes 32 of the interposer 30 and the second bonding portions of the electric cables 40 are bonded to each other using the second solders 39. For example, the second bonding portions where the second solders 39 are disposed are locally heated.

Local heating may be heating using a heater, heating using a laser, heating using a lamp or the like. Heating while applying a pressure may be performed when necessary. Besides applying heat energy, energy different from heat energy, for example, ultrasonic energy may be applied. For example, the second solders 39 are melted and bonded by applying laser heat. Laser heat can locally heat a minute region.

Even when local heating is applied, there is a risk that heat applied to the second bonding portions is transferred to the image pickup unit 10. However, in the image pickup apparatus 1, heat applied to the second bonding portions is transferred to the first bonding portions through elongated first electrodes 31.

Heat applied to the second bonding portions is minimally transferred to the first bonding portions and hence, there is no risk that reliability of the first bonding portions is deteriorated in the image pickup apparatus 1.

Further, the first penetration wires 10H of the image pickup unit 10 and the second penetration wires 30H of the interposer 30 differ from each other with respect to the positions in a direction orthogonal to the optical axis. In other words, the second penetration wires 30H are not disposed at the positions on imaginary extensions of the first penetration wires 10H in the optical axis direction.

Accordingly, even when the image pickup device 11 and the semiconductor devices 13 to 15 of the image pickup unit 10 are bonded to each other by soldering, heat applied to the second bonding portions is minimally transferred to the bonding portions of the stacked element.

With respect to the plurality of first penetration wires OH, it is sufficient that at least the first penetration wires 15H on which the external electrodes 10P are disposed be not disposed at the same position as the second penetration wires 30H. In a case where the rear surface 10SB is bisected into an upper region and a lower region and the first penetration wires 15H are disposed in the lower region, it is preferable that the second penetration wires 30H be disposed in the upper region.

Further, in a case where the first electrodes 31 extend to the position where the first electrodes 31 are brought into contact with the heat conductive resin 60, in other words, in a case where injecting of the heat conductive resin 60 is made in step S15 (resin disposing step) so that portions of the first electrodes 31 are brought into contact with the heat conductive resin 60, heat applied to the second bonding portions is radiated through the heat conductive resin 60 and hence, heat is further minimally transferred to the first bonding portions.

In the second bonding step, it is necessary to fix an outer peripheral surface of the image pickup unit 10 by holding using a jig, for example. In the image pickup apparatus 1, the outer peripheral surface of the image pickup unit 10 is covered by the heat conductive resin 60 and hence, at the time of bonding, the outer peripheral surface of the image pickup unit 10 is not held but the heat conductive resin 60 is held by the jig. Accordingly, there is no risk that the image pickup unit 10 which does not have a high mechanical strength is broken when the image pickup unit 10 is held by the jig.

As has been described above, the method of producing an image pickup apparatus according to this embodiment is a method of producing a small-sized and highly reliable image pickup apparatus.

Second Embodiment

An image pickup apparatus 1A for endoscope, a method of producing an image pickup apparatus 1A for endoscope, and an endoscope 9A according to a second embodiment are similar to the image pickup apparatus 1 for endoscope and the like according to the first embodiment and hence, the image pickup apparatus 1A and the like according to the second embodiment have substantially the same advantageous effects as the image pickup apparatus 1 and the like of the first embodiment. Accordingly, constitutional components having the same functions as the corresponding constitutional components in the first embodiment are given with identical symbols, and the description of these constitutional components is omitted.

Figure 8:
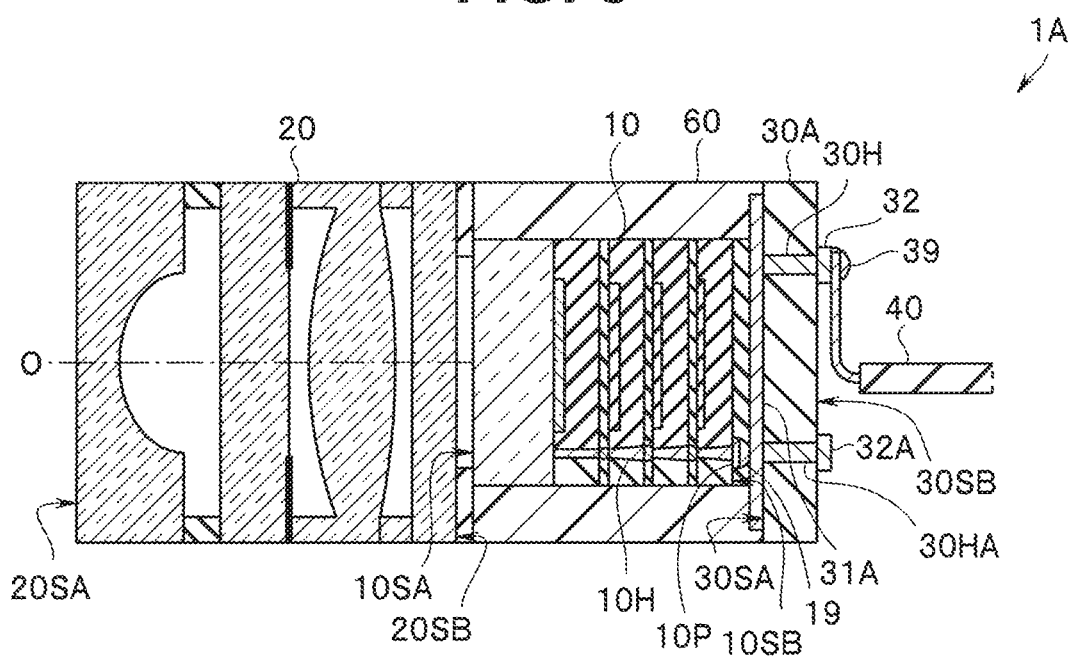
FIG. 8 is a cross-sectional view of an image pickup apparatus according to a second embodiment.
Figure 9:
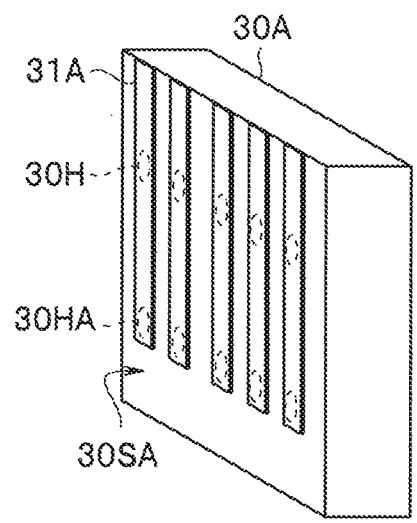
FIG. 9 is a perspective view of an interposer of the image pickup apparatus according to the second embodiment.
Figure 10:
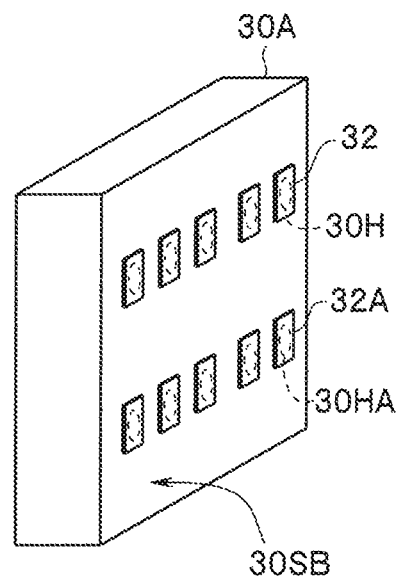
FIG. 10 is a perspective view of the interposer of the image pickup apparatus according to the second embodiment.

In the image pickup apparatus 1A shown in FIG. 8, FIG. 9, and FIG. 10, third electrodes 32A which are not bonded to electric cables 40 are disposed on a second main surface 30SB of an interposer 30A. The third electrodes 32A having the same configuration as second electrodes 32 are connected to first electrodes 31A via third penetration wires 30HA which are conductors.

The third penetration wires 30HA are disposed at the same position as the first penetration wires 10H in a direction orthogonal to an optical axis, that is, at the same position as the first bonding portions in the direction orthogonal to the optical axis. The first electrodes 31A not only connect the first penetration wires 10H and second penetration wires 30H to each other, but also may further extend from connection portions between the first electrodes 31A and the second penetration wires 30H to an end surface of a first main surface 30SA. The first electrodes 31A may extend to a position where portions of the first electrodes 31A are brought into contact with a heat conductive resin 60.

Figure 11:
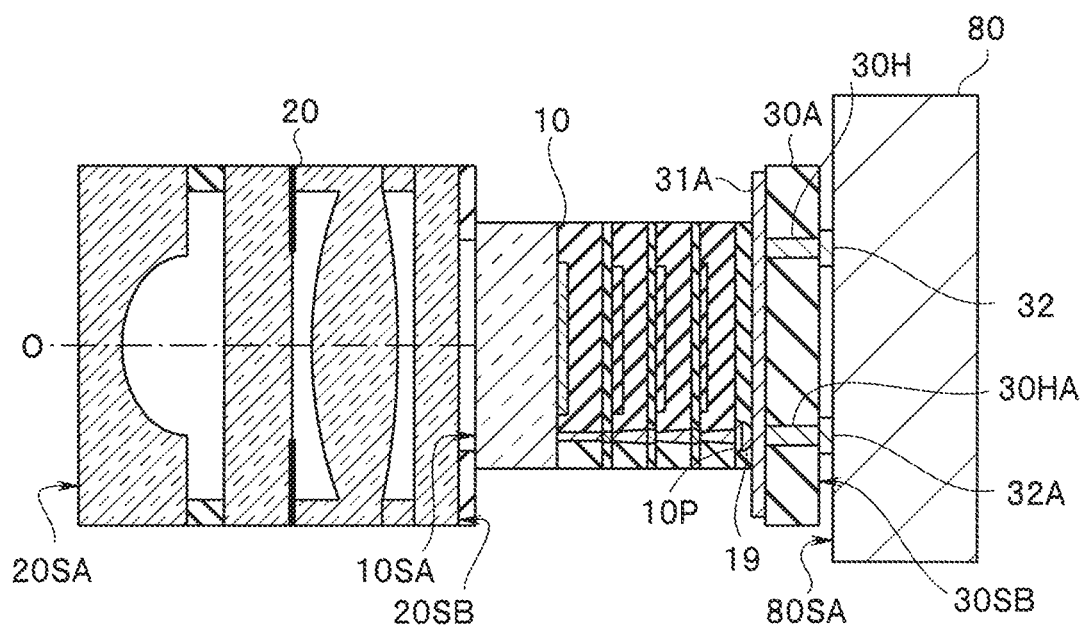
FIG. 11 is a cross-sectional view for describing a method of producing an image pickup apparatus according to the second embodiment.

As shown in FIG. 11, in a first bonding step (S14) of producing the image pickup apparatus JA, a heat generating surface 80SA of a heater 80 is brought into contact with the second main surface 30SB of the interposer 30A so that the second main surface 30SB is heated by the heat generating surface 80SA by face heating. Accordingly, heat is transferred not only to the second electrodes 32 and the second penetration wires 30H but also to the first solders 19 at the first bonding portions through the third electrodes 32A and the third penetration wires 30HA which are conductors.

As a conductor, it is preferable to use copper or aluminum which exhibits high heat conductivity and is inexpensive. In other words, the third electrodes 32A and the third penetration wires 30HA are conductors, and the third electrodes 32A and the third penetration wires 30HA are not provided for achieving electric conduction but are provided as heat transfer members for achieving heat transfer.

In the first bonding step (S14), the image pickup apparatus 1A can transfer heat of the heat generating surface 80SA to the first bonding portions more efficiently than the image pickup apparatus 1.

Figure 12:
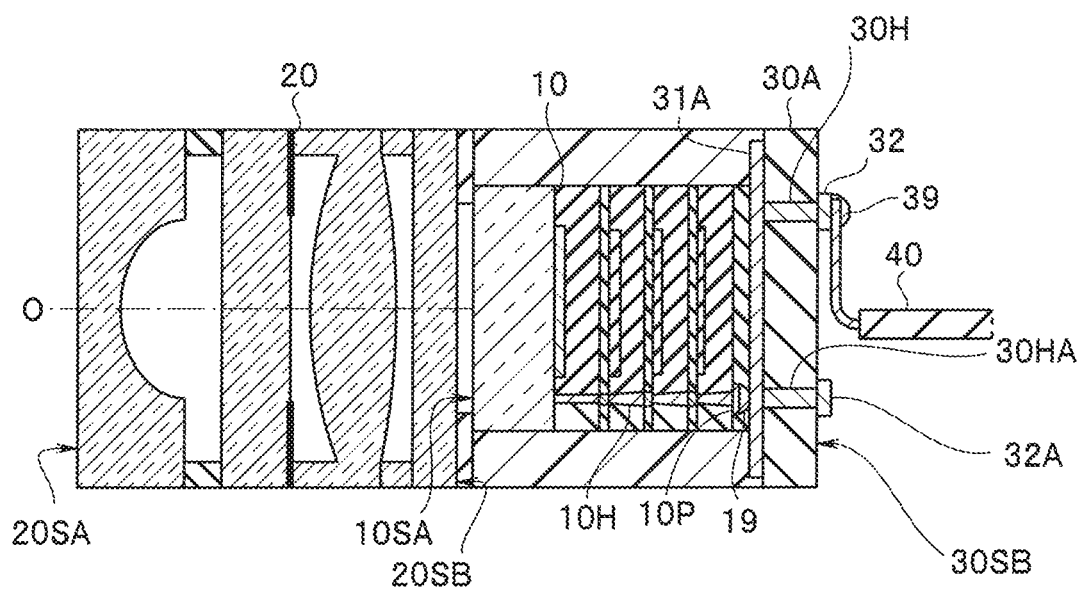
FIG. 12 is a cross-sectional view for describing the method of producing an image pickup apparatus according to the second embodiment.
Figure 13:
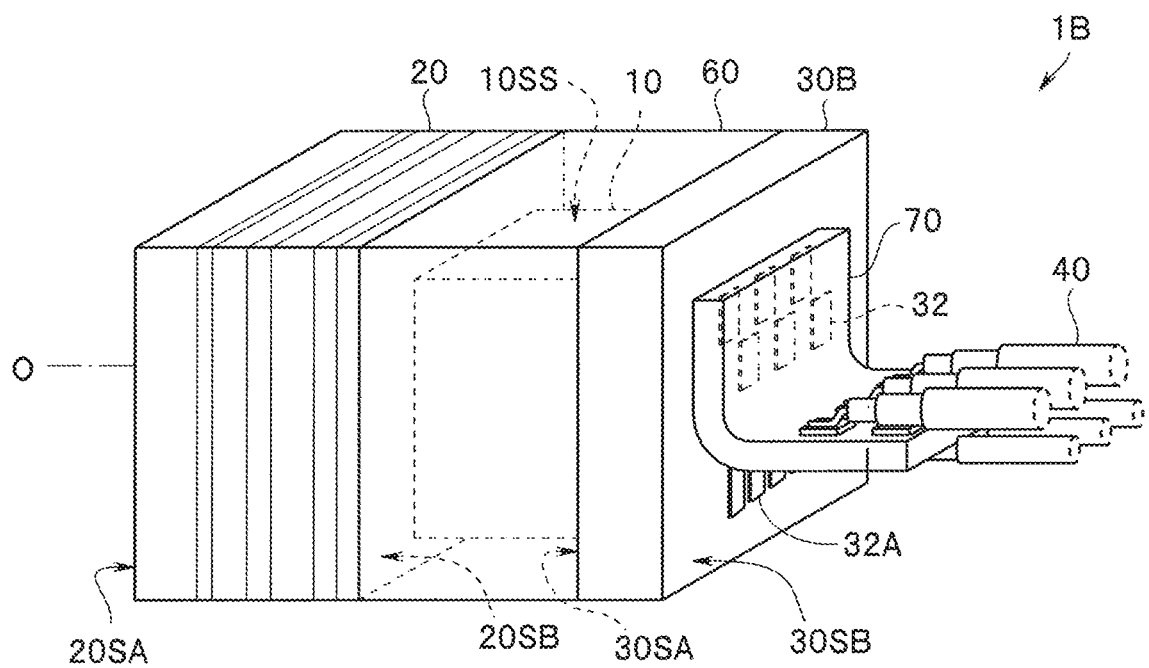
FIG. 13 is a perspective view of an image pickup apparatus according to a modification of the second embodiment.

In a second bonding step (S16) shown in FIG. 12, second solders 39 of the second bonding portions are locally heated. The first electrodes 31A extend to the position where the first electrodes 31A are brought into contact with the heat conductive resin 60 and hence, heat transferred to the first electrodes 31A is radiated through the heat conductive resin 60. Accordingly, heat applied to the second bonding portions is minimally transferred to the first bonding portions.

Further, in the image pickup apparatus 1A, the first bonding portions are connected to the third penetration wires 30HA via the first electrodes 31A. Heat which is transferred through the first electrodes 31A is immediately transferred to the third penetration wires 30HA and hence, a temperature of the first bonding portions is minimally increased. Accordingly, reliability of the first bonding portions is not lowered.

In other words, in the first bonding step (S14), the image pickup apparatus 1A transfers heat to the first bonding portions (first solders 19) more efficiently than the image pickup apparatus 1, and in the second bonding step (S16), the image pickup apparatus 1A transfers heat to the first bonding portions more minimally than the image pickup apparatus 1.

The third electrodes 32A and the third penetration wires 30HA have no particular functions in the image pickup apparatus 1A in the form of a completed product. However, the image pickup apparatus 1A can improve productivity in producing steps and can prevent lowering of reliability in the producing steps compared to the image pickup apparatus 1.

End surfaces of the third penetration wires 30HA may be regarded as the third electrodes 32A. In other words, even when the third electrodes 32A are not disposed, it is sufficient that a state is brought about where the end surfaces of the third penetration wires 30HA are exposed to the second main surface 30SB. In the first bonding step (S14), provided that a state is brought about where the end surfaces of the third penetration wires 30HA are brought into contact with the heater 80, heat of the heater 80 is transferred to the first solders 19 of the first main surface 30SA.

In place of the third penetration wires 30HA, conductor patterns disposed on a side surface of the interposer may be used. In other words, the conductor which transfers heat of the heater 80 which is brought into contact with the second main surface 30SB to the first solders 19 of the first main surface 30SA may be either side surface wires or the penetration wires and the side surface wires.

Modification of Second Embodiment

An image pickup apparatus 1B for endoscope, a method of producing an image pickup apparatus 1B for endoscope, and an endoscope 9B according to a modification of the second embodiment are similar to the image pickup apparatus 1A for endoscope and the like according to the second embodiment and hence, the image pickup apparatus 1B and the like according to the modification of the second embodiment have substantially the same advantageous effects as the image pickup apparatus 1A and the like according to the second embodiment. Accordingly, constitutional components having the same functions as the corresponding constitutional components in the second embodiment are given with identical symbols, and the description of these constitutional components is omitted.

As has been described above, in the image pickup apparatus according to the embodiments, an object which are bonded to second electrodes 32 of an interposer 30B may be a wiring board. In the image pickup apparatus 1B according to the modification of the second embodiment shown in FIG.

13 further includes a wiring board 70. For example, electrodes (not shown in the drawing) of the flexible wiring board 70 which includes a substrate made of polyimide are bonded to the second electrodes 32 of the interposer 30B. Electric cables 40 are bonded to the wiring board 70.

In the image pickup apparatus 1B, heat generated in a second bonding step of bonding the wiring board 70 to the interposer 30B by soldering does not give an adverse effect to bonding portions bonded with external electrodes 10P of an image pickup unit 10 in a first bonding step.

Needless to say, the endoscopes 9A, 9B respectively having the image pickup apparatus 1A according to the second embodiment and the image pickup apparatus 1B according to the modification of the second embodiment acquire advantageous effects of the respective image pickup apparatuses 1A, 1B in addition to advantageous effects acquired by the endoscope 9.

Third Embodiment

An image pickup apparatus 1C for endoscope and a method of producing an image pickup apparatus 1C for endoscope according to the third embodiment are similar to the image pickup apparatuses 1, 1A, 1B for endoscope and the like according to the first embodiment, the second embodiment, and the modification of the second embodiment. Accordingly, constitutional components having the same functions as the corresponding constitutional components in the first embodiment, the second embodiment, and the modification of the second embodiment are given with identical symbols, and the description of these constitutional components is omitted.

Figure 14:
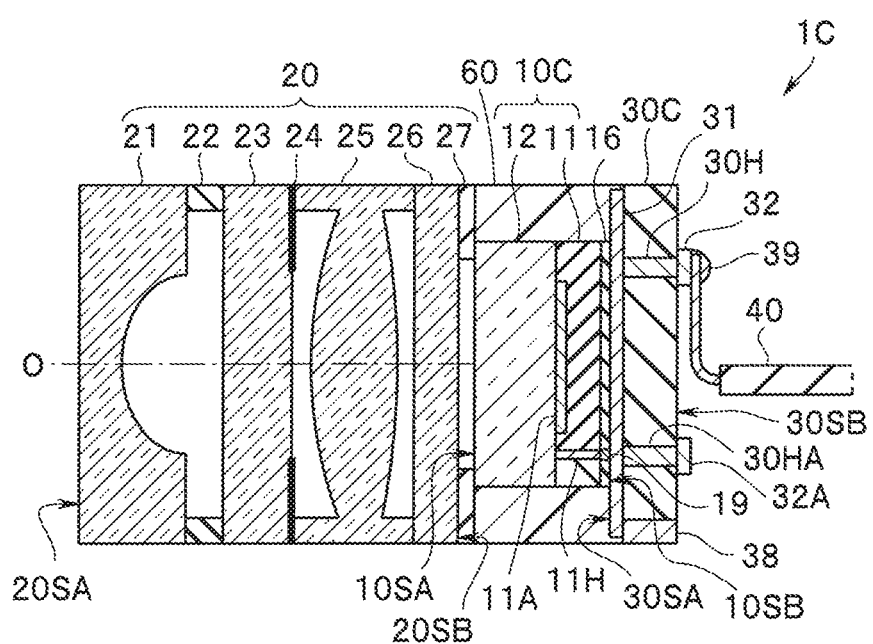
FIG. 14 is a cross-sectional view of an image pickup apparatus according to a third embodiment.

In the image pickup apparatus 1C shown in FIG. 14, an image pickup unit 10C is formed of an image pickup device 11 to which a cover glass 12 adheres. As has been described previously, the cover glass 12 adheres to a light receiving surface 10SA using an adhesive agent and hence, a mechanical strength of the image pickup unit 10C is not so high.

The image pickup apparatus 1C includes, in addition to third penetration wires 30HA provided for transferring heat, conductor patterns 38 disposed on a side surface of an interposer 30C. The conductor patterns 38 are heat transfer patterns connected to first electrodes 31A.

The image pickup apparatus 1C acquires substantially the same advantageous effects as the image pickup apparatuses 1, 1A, 1B and the like.

The present invention is not limited to the above-mentioned embodiments and the like, and the present invention can be altered or modified without departing from the gist of the present invention.

What is claimed is:

1. An image pickup apparatus for an endoscope, comprising:
    an optical unit formed by stacking a plurality of optical members, the optical unit including an incident surface and an emitting surface;
    an image pickup unit comprising an image sensor, the image sensor having a light receiving surface, the image pickup unit having a front surface opposedly facing the emitting surface and a rear surface on a side opposite to the front surface, wherein an external electrode is disposed on the rear surface, the external electrode being connected to the light receiving surface via a first penetration wire penetrating between the front and rear surfaces;
    an interposer including a first main surface opposedly facing the rear surface, the interposer further including a second penetration wire disposed in a through hole extending from the first main surface to a second main surface on a side opposite to the first main surface, wherein a first electrode is disposed on the first main surface, a second electrode connected to the first electrode via the second penetration wire is disposed on the second main surface, and the first electrode is bonded to the external electrode; and
    an electric cable or a wiring board bonded to the second electrode by soldering,
    wherein an outer size of the image pickup unit is smaller than an outer size of each of the optical unit and the interposer in a direction orthogonal to an optical axis, and the image pickup unit is housed in a space disposed on an imaginary extension of the optical unit in an optical axis direction,
    the image pickup apparatus further comprises a heat conductive resin with which a portion among the emitting surface, the first main surface, and a side surface of the image pickup unit is filled, and
    the first electrode having an elongated shape with a first portion and a second portion, wherein the first portion is connected to the external electrode and the second portion is connected to the second penetration wire, the first electrode including an extending portion that extends from at least one of the first portion or the second portion, the extending portion being configured to directly contact the heat conductive resin.

2. The image pickup apparatus for the endoscope according to claim 1, wherein the image pickup unit includes a stacked element formed by stacking a plurality of semiconductor devices including the image sensor.

3. The image pickup apparatus for the endoscope according to claim 1, wherein the image pickup unit further comprises a cover glass adhered to the image sensor.

4. The image pickup apparatus for the endoscope according to claim 1, wherein heat conductivity of the heat conductive resin is more than 1 W/mK.

5. The image pickup apparatus for the endoscope according to claim 1, wherein a position of the first penetration wire and a position of the second penetration wire differ from each other in the direction orthogonal to the optical axis.

6. The image pickup apparatus for the endoscope according to claim 1, wherein
    the external electrode and the first electrode are bonded to each other using a first solder, and
    the electric cable or the wiring board and the second electrode are bonded to each other using a second solder.

7. The image pickup apparatus for the endoscope according to claim 6, wherein a melting point of the second solder is lower than a melting point of the first solder.

8. The image pickup apparatus for the endoscope according to claim 1, wherein the interposer further comprising a third electrode disposed on the second main surface, the third electrode is connected to the first electrode via a conductor and is not bonded to the electric cable or the wiring board on the second main surface.

9. The image pickup apparatus for the endoscope according to claim 1, wherein the outer size of the optical unit, and the outer size of each of the heat conductive resin and the interposer are equal in the direction orthogonal to the optical axis.

\* \* \* \* \*